United States Patent [19]

Wheeler et al.

[11] Patent Number: 5,583,267
[45] Date of Patent: Dec. 10, 1996

[54] BIOCATALYTIC PROCESS FOR PREPARING TETRAALKYLBIPHENOLS

[75] Inventors: Thurman M. Wheeler; Mark K. Morehart; Gregory Kaplan, all of Columbus; Alexander R. Pokora, Pickerington, all of Ohio

[73] Assignee: Enzymol International, Inc., Columbus, Ohio

[21] Appl. No.: 379,202

[22] Filed: Jan. 27, 1995

[51] Int. Cl.[6] .................................................. C07C 37/00
[52] U.S. Cl. ............................................ 568/730; 568/717
[58] Field of Search ..................................... 568/717, 730

[56] References Cited

U.S. PATENT DOCUMENTS

| | | | |
|---|---|---|---|
| 3,812,193 | 5/1974 | Randell et al. | 568/730 |
| 3,929,913 | 12/1975 | Maggioni | 568/730 |
| 4,101,561 | 7/1978 | Rutledge | 568/730 |
| 4,950,808 | 8/1990 | Kowalezik et al. | 568/730 |

FOREIGN PATENT DOCUMENTS 0140034  8/1983  Japan ..................... 568/730

*Primary Examiner*—Werren B. Lone
*Attorney, Agent, or Firm*—Thompson Hine & Flory

[57] ABSTRACT

In accordance with the present invention, tetraalkylbisphenols are prepared by biocatalytic dimerization of di-(lower alkyl)-substituted phenols in the presence of peroxidase enzyme and peroxide. Three reaction pathways to the desired diols are provided.

22 Claims, No Drawings

BIOCATALYTIC PROCESS FOR PREPARING TETRAALKYLBIPHENOLS

BACKGROUND OF THE INVENTION

The present invention relates to an improved process for preparing tetraalkyl-biphenols by the reaction of a di(lower alkyl)-substituted phenol with a peroxidase enzyme and peroxide, and, more particularly, by the reaction of 2,4- or 2,6-dimethylphenol in the presence of soybean peroxidase and hydrogen peroxide.

Commercial reactions for preparing tetraalkyl substituted diols are known, however, the reactions are undesirable because they are inefficient and extremely inconvenient to carry out in an industrial setting. For example, Japanese Kokai Tokyo Koho JP 04338347 AZ describes the preparation of 3,3',5,5'-tetramethyl-4,4'-biphenol in little over 60% yield by oxidative dimerization of appropriate phenols in a molten state in the presence of an oxygen-containing gas and sodium hydroxide. The reaction product contained greater than 35% unwanted monomer. Japanese Kokai Tokkyo Koho JP 03275639 AZ describes the oxidative coupling of 2,6-xylenol in the presence of copper acetate, sodium bicarbonate, sodium dodecyl sulfate and sodium sulfate to give 3,3',5,5'-tetramethyl-4,4'-biphenol. Japanese Kokai Tokkyo Koho JP 03275638 AZ describes the preparation of 3,3',5,5'-tetramethyl-4,4'-biphenol by the oxidative dimerization of 2,6-xylenol in the presence of metal catalysts such as copper acetate. The prior art reactions are undesirable because they are generally inefficient and the metals or metal salts must be removed and either recycled or properly disposed of. Accordingly, there exists a need for a convenient and inexpensive method for preparing tetraalkylbiphenols from di(lower alkyl)substituted phenols.

SUMMARY OF THE INVENTION

In accordance with the present invention, tetraalkylbiphenols are prepared by the biocatalytic dimerization of di(lower alkyl)-substituted phenols in the presence of a peroxidase enzyme and a peroxide. Three reaction pathways to the desired diols are provided. Processes in accordance with the invention may involve all or individual ones of these pathways. Each pathway constitutes an embodiment of the invention.

In one embodiment of the invention, the process is carried out in an aqueous medium using 2,6-dialkylphenol and involves two stages. The first stage of the reaction includes the biocatalytic oxidation of the phenol and results in the production of the desired tetraalkylbiphenol, as well as a corresponding tetraalkylquinone. The ratio of the biphenol to the quinone will vary depending on the reactants and conditions used. The second stage includes the reduction of the quinone to the desired tetraalkylbiphenol. In the second stage, if the starting phenol is used as the reducing agent for the quinone, as the quinone is reduced to the desired biphenol, the phenol is oxidized. The oxidized phenol also reacts with itself to generate the tetraalkylbiphenol. Thus the biphenol can be obtained by direct biocatalytic oxidative coupling of the phenol, as well as via production and reduction of the quinone, and chemical oxidative coupling of the phenol upon reduction of the quinone.

In another embodiment, the process is carried out using a 2,4-dialkylphenol. The biocatalytic oxidation of this monomer yields the tetraalkylbiphenol without production of the quinone.

Accordingly, one manifestation of the invention is the production of tetraalkylbiphenols by a process which comprises reacting a 2,4 or 2,6-dialkylphenol with a peroxidase enzyme in the presence of a peroxide in an aqueous medium to oxidatively couple the phenols. In one process in accordance with the invention, the phenol monomer is dimerized to form the biphenol and the corresponding quinone in the first stage and, subsequently, a reducing agent is added to the medium and the quinone is reacted with the reducing agent at a higher temperature in a second stage to convert the quinone to the desired diol. In the preferred embodiment of the invention, the reducing agent is the same phenol from which the quinone is derived. In the preferred embodiment all three pathways generate the desired diol. The process can be performed without a separate addition of reducing agent if the phenol monomer is only partially reacted in the first stage. This yields a mixture of quinone, diol and unreacted phenol monomer. Ideally, the oxidation of the phenol is stopped such that molar ratio of quinone to unreacted phenol is about 1:2, the ratio stoichiometrically required to reduce the quinone. In the second stage, the mixture of quinone and unreacted phenol monomer is further reacted at a higher temperature to convert the quinone to the desired diol. The oxidized phenol also couples to form the diol in this stage.

It is, therefore, an object of the present invention to provide an improved process for the preparation of a tetraalkyl-substituted biphenol by the biocatalytic dimerization of a di(lower alkyl)-substituted phenol in the presence of a peroxidase enzyme, and a peroxide in an aqueous medium.

It is another object of the present invention to provide an improved method for the preparation of a tetraalkyl-substituted biphenol in which the by-product quinone is converted to the biphenol. Preferably by reduction with the starting phenol.

It is also an object of the present invention to provide an improved method for the preparation of a tetraalkyl-substituted biphenol by the biocatalytic oxidative coupling of a di(lower alkyl)-substituted phenol in the presence of a peroxidase enzyme, and a peroxide in an aqueous medium.

The process of the present invention is also useful in preparing biphenols of 2,4 and 2,6 diarylphenols such as 2,4 and 2,6 diphenylphenol.

DETAILED DESCRIPTION OF THE INVENTION

In carrying out the present invention, a 2,4- or a 2,6-dialkylphenol wherein the alkyl group is a $C_1$ to $C_6$ alkyl group is reacted with a peroxidase enzyme in the presence of a peroxide.

In this embodiment of the invention, the phenol monomer is partially reacted to form the biphenol and quinone and the balance of the monomer remains in the reaction mixture for reduction of the quinone at a higher temperature in the second stage. The first stage involves the production of the tetraalkylbiphenol, a tetraalkyl-substituted quinone which results from the oxidative dimerization of the phenolic monomer and oxidation of a portion of the biphenol to the quinone. After this reaction, the temperature is increased to a temperature where the unreacted phenol converts the quinone to the desired tetraalkyl-substituted biphenol. In this reaction, two moles of phenol is necessary to reduce all the quinone. The first stage reaction can be carried out until there is a ratio of about 1 mole of quinone to 2 moles of unreacted phenol in the reaction mixture or additional phenol can be added to the reaction mixture to bring the ratio to 1:2. At this point, the temperature is raised such that the unreacted phenol reacts with the quinone reducing it to the desired tetraalkyl-substituted biphenyl diol.

In the second embodiment, the initial charge of phenol monomer is completely or essentially completely converted to the biphenol and the quinone in the first stage and additional phenol monomer or another reducing agent is added at the second stage and the temperature is increased for reduction of the quinone produced in the first stage to provide the desired biphenol. In this second embodiment, the first stage involves the depletion of the di(lower alkyl)-substituted phenol to form the biphenol and the tetraalkyl-substituted quinone. Upon completion of the reaction, additional phenol monomer is added to the reaction mixture in an amount to provide a molar ratio of quinone to phenol of about 1:2. When other reducing agents are used they are employed in an equivalent amount. The temperature is then raised to a point at which the quinone is reduced to the desired tetraalkyl-substituted biphenol.

Those skilled in the art will recognize that a hybrid of the first and second embodiments will often be used. That is, the first stage reaction will be carried to a point at which the ratio of quinone to unreacted phenol may be greater than 1:2 and the second stage of the reaction will include the step of adding additional phenol to the reaction system to bring the ratio to approximately the 1:2 ratio required to reduce quantitatively the quinone.

The phenol monomers useful in the present invention include 2,6- and 2,4-dialkyl-substituted phenol. The latter does not form quinone. The alkyl groups have 1 to 6 carbon atoms, preferably such alkyl groups are straight chained and, more preferably, the alkyl groups contain about 1 to 3 carbon atoms. The alkyl groups are most typically methyl groups. In an especially preferred aspect of the invention, the phenol is a 2,6-dimethyl phenol and the resulting diol is 3,3',5,5'tetramethylbiphenyl-4,4'-diol. Reaction of the 2,4-dimethylphenol yields 3,3',5,5'-tetramethylbiphenyl-2,2'-diol. Those skilled in the art will also appreciate that while the alkyl groups in a monomer are typically the same, monomers having two different alkyl groups and mixtures of different dialkyl phenols may be reacted as well.

The inventive process can also be used to couple 2,4 or 2,6 diarylphenols in which the aryl groups have 6 to 10 carbon atoms such as phenyl, benzyl, etc.

The concentration of the phenol monomer is not particularly critical. Typically, the phenol monomer will be used in amounts up to about 3 molar and, preferably, about 2.2 to 3 molar will be sufficient. Higher concentrations tend to be too viscous to stir and react effectively.

A variety of peroxidases can be used in the present invention. The most preferred peroxidase is soybean peroxidase because it is stable at the higher temperatures required to form the quinone. However, other peroxidases may also be useful such as horseradish peroxidase and peroxidases from other legumes such as peroxidases from peas, guar, beans, garbanzo beans and runner beans. It is also believed that peroxidases from rice and certain malvaceous plants, such as cotton may be useful and that bacterial peroxidases are also useful.

The amount of enzyme used to make the tetraalkylbiphenol will depend on its activity with respect to the particular substrate at the reaction temperatures used. Generally, the present invention appears to require a higher amount of enzyme than used in the enzyme catalyzed oxidation for resin-forming reaction described in our U.S. Pat. No. 5,188,953. It has been found that the amount of enzyme useful in the present invention can range from about 50 to 300 purpurogallin units. It is generally desirable to prepare an enzyme solution at an approximate concentration such that it can be added in an approximately equal volume to the solution of the phenol monomer, but this is not necessary and, in many cases, may vary greatly.

The peroxide used in the present invention is typically hydrogen peroxide, but other peroxides may be used. Examples of other potentially useful peroxidases include methyl peroxide, ethyl peroxide, etc.

The peroxide is reacted in a total amount of about 0.1 to 2.5 moles per mole phenol monomer and, more typically, about 0.1 to 1.0 mole per mole phenol. Depending upon its nature, it may be reacted neat or as a solution. Because high concentration of peroxide will inhibit the reaction, in the preferred embodiments of the invention, hydrogen peroxide is dissolved in water in a concentration of about 1 mM to 10M and then added to the reaction medium at a rate which decreases from an initial rate as the amount of phenol monomer decreases as described next. The initial rate of addition (moles/min.) of the peroxide solution is set at about twice the average reaction rate. Typically, the peroxide is initially added at a rate of about 7.0 millimoles (per mole of phenol in the reaction)/min. and, thereafter, the rate of addition is adjusted downwardly for the decrease in the rate of reaction which accompanies the reaction of the phenol and the lower phenol concentration. The rate of downwardly adjustment is controlled such that the peroxide concentration does not exceed 3 to 12 millimolar and, preferably, about 3 to 5 millimolar.

The reaction is conducted in an aqueous medium. The term "aqueous medium" as used herein means a medium consisting of water or a medium containing a mixture of water and organic solvent. Where the medium is a mixture of water and an organic solvent, the organic solvent is typically present in an amount up to about 60% and preferably up to 30%. Representative examples of useful organic solvents include hexane, trichloromethane, methyl ethyl ketone, ethyl acetate, butanol, ethanol, methanol, dioxane, acetonitrile, tetrahydrofuran (THF), dimethyl formamide methyl formate, acetone, n-propanol, isopropanol, t-butyl alcohol, etc. A medium consisting solely of water has been found to be particularly useful in the present invention.

Since the dialkyl-substituted phenols useful in the present invention are not soluble in water, an elevated temperature of about 35° C. to 60° C. and more typically 45° C. to 60° C. is used to melt the phenol monomer and disperse it in the aqueous medium. Once the monomer is melted, it is dispersed in the water medium by thorough mixing. It may be desirable to add a surfactant to the monomer/water reaction medium in order to improve the dispersion of the monomer and thereby improve the reaction. In other instances, it may be desirable to use a mixture of water and organic solvent as the reaction medium but, presently, it is preferred to use a medium consisting solely of water.

Reduction of the quinone is typically accomplished at temperatures of about 60° C. to 120° C. The reaction is very slow at the lower temperatures so temperatures of 100° C. to 120° C. are preferred. While it is generally desirable and preferred to use the monomer as the reducing agent for the quinone, it will be appreciated by those skilled in the art that any compound capable of reducing the quinone can be used in this stage of the reaction. Examples of other reducing agents include phenol, 2,4-di-t-butylphenol, 2,6-di-t-butylphenol, p-octylphenol, p-t-butylphenol, sodium borohydride, sodium dithionite, etc. One advantage of using the starting monomer is that the reduced monomer reacts to form more biphenol and the excess monomer is easily removed from the reaction.

When the monomer is used as the reducing agent, the reaction typically yields the tetraalkyl-substituted biphenol in admixture with polyphenylene oxide (PPO) as a by-product and some unreacted monomer. The PPO can be easily removed by toluene extraction and any excess monomer is removed by steam distillation to provide the desired product in excellent purity and yield.

The tetraalkyl-substituted biphenols prepared in accordance with the present invention are useful in a variety of applications such as in making epoxy resins, flame retardants, antioxidants, polyesters, polycarbonates, and in other applications in which aromatic diols are used.

The invention is illustrated in more detail by the following non-limiting examples:

EXAMPLE 1

Add 122 grams of 2,6-dimethylphenol to 160 ml of a soybean peroxidase solution (33,500 ppu units) while stirring at 48° C. To the reaction mixture, add 33 ml of 35% hydrogen peroxide at a constant rate over six hours. Upon completion of the addition of the hydrogen peroxide, the reaction mix is heated at 100° C. for 1.5 hours. The product was collected by filtration and washed twice with 200 ml of toluene for 30 minutes at 30° C. to remove unreacted monomer and any polyphenylene oxide. After drying, 90 grams of tetramethyl biphenol, 21 grams of monomer and 10 grams of polyphenylene oxide were collected.

EXAMPLE 2

Add 122 grams of 2,6-dimethylphenol dissolved in 60 ml of isopropanol to 240 ml of a soybean peroxidase solution (36,600 ppu units) while stirring at 48° C. To the reaction mixture, add 80 ml of 35% hydrogen peroxide at the rates indicated below. Note that between the times indicated in the table, the addition is decreased about linearly to the next rate at the next time indicated.

TABLE

| Time | $H_2O_2$ (millimoles/min) |
| --- | --- |
| 0 | 7 |
| 1 hr. | 4.7 |
| 2 hr. | 2.5 |
| 3 hr. | 1.6 |
| 4 hr. | 2.5 |
| 5 hr. | 2.0 (constant until depleted) |

Upon completion of the addition of the hydrogen peroxide, the isopropanol was removed by distillation. The reaction mixture contains 52 grams of tetramethyl quinone dimer, 34 grams of tetramethyl biphenol and 36 grams of polyphenylene oxide. 52 grams of 2,6-dimethylphenol were added to the reaction mix and heated for 1.5 hours at 100° C. The product was collected by filtration and washed twice with 300 ml of toluene at 30° C. for 30 minutes. After drying, 140 grams of tetramethyl biphenol and 34 grams of polyphenylene oxide were collected.

EXAMPLE 3

2,4-Dimethylphenol (100 gm, 0.82 mole), ethyl alcohol (175 mL), water (175 mL) and soybean peroxidase (175 mL, 43,750 PPU) were added to a water-jacketed three neck RB flask equipped with mechanical stirrer. While stirring and heating to 50° C., hydrogen peroxide (35%, 52 mL) was added according to a ramping pump rate of 0.57 mL/min over 3 hr. After the addition of peroxide was completed, the reaction was cooled to room temperature, then the white solid precipitate was collected by filtration. After drying, 80 gm. of 2,4-dimethylphenol dimer was obtained. The solvent remaining contained about 20 gm. of 2,4-dimethylphenol monomer.

Having described the invention in detail and by reference to preferred embodiments thereof, it will be apparent that modifications and variations are possible without departing from the scope of the invention defined in the appended claims.

What is claimed is:

1. A process for preparing tetraalkyl-substituted biphenol which comprises reacting a 2,4- or 2,6-dialkyl substituted phenol in which the alkyl groups contain 1 to 6 carbon atoms with a peroxidase enzyme in the presence of a peroxide in an aqueous medium to yield a tetraalkyl-substituted biphenol by oxidative coupling of the 2,4- or 2,6-dialkyl substituted phenol.

2. The process of claim 1 wherein said phenol is 2,6-dimethylphenol.

3. The process of claim 1 wherein said phenol is 2,4-dimethylphenol.

4. The process of claim 1 wherein said aqueous medium is water.

5. The process of claim 1 wherein said aqueous medium is a mixture of water and a solvent.

6. The process of claim 3 wherein said peroxidase is soybean peroxidase.

7. A process for preparing tetraalkyl-substituted biphenol which comprises reacting a 2,6-dialkyl substituted phenol in which the alkyl groups contain 1 to 6 carbon atoms with a peroxidase enzyme in the presence of a peroxide in an aqueous medium to yield a tetraalkyl-substituted quinone, and reducing the quinone to obtain a tetraalkyl-substituted biphenol.

8. The process of claim 7 wherein the step of reducing the quinone is carried out by reacting the quinone with the 2,6-dialkyl substituted phenol.

9. The process of claim 8 wherein the reaction of the 2,6-dialkyl substituted phenol to yield the quinone is carried out at a temperature of about 35° to 60° and the reduction of the quinone to said diol is carried out at a temperature of about 60° to 120° C.

10. The process of claim 9 wherein after obtaining the quinone, additional phenol is added to the aqueous medium and said quinone is converted to said diol by reduction at a temperature of about 60° to 120° C.

11. The process of claim 7 wherein said peroxidase is soybean peroxidase.

12. The process of claim 11 wherein said peroxide is hydrogen peroxide.

13. The process of claim 7 wherein said aqueous medium is a mixture of water and an organic solvent.

14. The process of claim 7 wherein said aqueous medium consists of water.

15. The process of claim 7 wherein said phenol is present in the medium in an amount of about 2.2 to 3 molar.

16. The process of claim 15 wherein said peroxidase is present in an amount of about 50 to 300 units per mole of phenol.

17. A process for preparing 3,3',5,5'tetramethyl-biphenyl -4,4'-diol which comprises reacting 2,6-dimethyl phenol with soybean peroxidase in the presence of hydrogen peroxide at a temperature of about 45° to 60° C. in an aqueous medium to form 3,3', 5,5'tetramethyl-biphenyl-4,4'-diol and 3,3',5,5'tetramethylquinone in a first stage and thereafter in a second stage, reducing said 3,3',5,5'tetramethylquinone to 3,3',5,5'tetramethyl-biphenyl-4,4'-diol with said 2,6-dimethyl phenol at a temperature of about 100° to 120° C.

18. The process of claim 17 wherein after forming the quinone, additional 2,6-dimethylphenol is added to the reaction.

19. A process for preparing a tetraaryl-substituted biphenol in which the aryl groups contain 6 to 10 carbon atoms which comprises reacting a 2,4 or 2,6 diarylphenol with a peroxidase enzyme in the presence of peroxide in an aqueous medium to yield a tetraaryl-substituted biphenol.

20. A process for reducing a tetraalkyl-substituted quinone to the corresponding tetraalkyl-substituted biphenol which comprises reducing said quinone with a phenol in an aqueous medium at a temperature of about 60° to 120° C.

21. The process of claim 20 wherein said quinone is present as a mixture of said quinone and said biphenol and said quinone is reduced with said phenol.

22. The process of claim 20 wherein said quinone is the reaction product of a dialkylphenol and said quinone is reduced by reaction with said dialkylphenol.

\* \* \* \* \*

UNITED STATES PATENT AND TRADEMARK OFFICE
CERTIFICATE OF CORRECTION

PATENT NO. : 5,583,267
DATED : December 10, 1996
INVENTOR(S) : Thurman M. Wheeler et al.

It is certified that error appears in the above-indentified patent and that said Letters Patent is hereby corrected as shown below:

In the ABSTRACT, lines 1 and 2, "tetraalkylbisphenol" should be -- tetraalkylbiphenol --.

In claim 6, line 1, "3" should be --1--.

Signed and Sealed this

Twenty-second Day of April, 1997

Attest:

BRUCE LEHMAN

*Attesting Officer*

*Commissioner of Patents and Trademarks*

REEXAMINATION CERTIFICATE (3675th)

United States Patent [19]

Wheeler et al.

[11] B1 5,583,267
[45] Certificate Issued Nov. 24, 1998

[54] BIOCATALYTIC PROCESS FOR PREPARING TETRAALKYLBIPHENOLS

[75] Inventors: Thurman M. Wheeler; Mark K. Morehart; Gregory Kaplan, all of Columbus; Alexander R. Pokora, Pickerington, all of Ohio

[73] Assignee: Enzymol Internaional, Columbus, Ohio

Reexamination Request:
No. 90/004,862, Dec. 30, 1997

Reexamination Certificate for:
Patent No.: 5,583,267
Issued: Dec. 10, 1996
Appl. No.: 379,202
Filed: Jan. 27, 1995

Certificate of Correction issued Apr. 22, 1997.

[51] Int. Cl.$^6$ .................................................... C07C 37/00
[52] U.S. Cl. ........................... 568/730; 435/156; 568/717
[58] Field of Search ........................... 568/717, 730

[56] References Cited

U.S. PATENT DOCUMENTS

| | | | |
|---|---|---|---|
| 4,647,952 | 3/1987 | Pokora et al. | 346/210 |
| 4,900,671 | 2/1990 | Pokora et al. | 435/156 |
| 5,147,793 | 9/1992 | Johnson et al. | 435/156 |

OTHER PUBLICATIONS

Klibanov et al. "Enzymatic Removal of Toxic Phenols and Analines from Waste Water" J. Applied Biochem. 2, pp. 414–421 (1980).

*Primary Examiner*—Gary Geist

[57] ABSTRACT

In accordance with the present invention, tetralkylbisphenols are prepared by biocatalytic dimerization of di-(lower alkyl)-substituted phenols in the presence of peroxidase enzyme and peroxide. Three reaction pathways to the desired diols are provided.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 7-18 and 20-22 are confirmed.

Claims 1-6 and 19 are cancelled.

* * * * *